United States Patent [19]

Shillington

[11] Patent Number: 5,402,887
[45] Date of Patent: Apr. 4, 1995

[54] NEEDLE EXTRACTOR FOR DISPOSABLE CONTAINERS

[75] Inventor: Richard A. Shillington, Leucadia, Calif.

[73] Assignee: Med-Safe Systems, Inc., Oceanside, Calif.

[21] Appl. No.: 946,523

[22] Filed: Sep. 16, 1992

[51] Int. Cl.⁶ .............................................. B65D 83/10
[52] U.S. Cl. ..................................... 206/366; 206/370
[58] Field of Search ................ 206/366, 370; 220/908; 604/192, 198; 29/240

[56] References Cited

U.S. PATENT DOCUMENTS

| | | | |
|---|---|---|---|
| 4,375,849 | 3/1983 | Hanifl | 206/366 |
| 4,466,538 | 8/1984 | Gianni | 206/366 |
| 4,494,652 | 1/1985 | Nelson et al. | 206/370 |
| 4,667,821 | 5/1987 | Shillington | 206/366 |
| 4,738,362 | 4/1988 | Burns et al. | 206/366 |
| 4,842,138 | 6/1989 | Sandel et al. | 206/370 |
| 4,844,245 | 7/1989 | Bennett | 206/366 |
| 4,867,309 | 9/1989 | Germain | 206/366 |
| 4,875,265 | 10/1989 | Yoshida | 29/240 |
| 4,892,191 | 1/1990 | Nakamura | 206/366 |
| 4,955,477 | 9/1990 | Bruno | 206/366 |
| 4,984,686 | 1/1991 | Shillington | 206/366 |
| 4,995,871 | 2/1991 | Sasaki et al. | 604/110 |
| 5,031,767 | 7/1991 | Bruno | 206/370 |
| 5,046,612 | 9/1991 | Mostarda et al. | 206/365 |
| 5,046,613 | 9/1991 | Baudry et al. | 206/366 |

*Primary Examiner*—David T. Fidei
*Attorney, Agent, or Firm*—Baker, Maxham, Jester & Meador

[57] ABSTRACT

A disposable container closure assembly includes a needle removal slot having gear teeth along one side thereof for engaging flutes on a needle hub for rotating the needle relative to a non-rotatable holder passed therealong.

20 Claims, 1 Drawing Sheet

NEEDLE EXTRACTOR FOR DISPOSABLE CONTAINERS

BACKGROUND OF THE INVENTION

The present invention relates to needle removal devices for syringes, and pertains particularly to an improved needle detacher for quick and easy removal of needles from syringes.

Disposable containers have been developed in recent years which provide a reasonably high degree of security for disposable sharps articles and materials from hospitals and clinics. Many of these articles, such as needles and surgical blades known as sharps, and other similar articles and materials, must be disposed of in a manner to keep them out of the hands of unauthorized persons and to keep them from being reused. These containers are designed to prevent the removal of materials from the container under ordinary circumstances. It is desirable in most instances to remove the needle from syringes and other such instruments prior to disposal or for separate disposal.

One secure container of the aforementioned type is that disclosed in prior U.S. Pat. No. 4,502,606, issued Mar. 5, 1985, and directed to a locking closure for disposable containers. These containers, are also usually provided with needle removal tools in the form of one or more slots which act as a wrench for removal of the needles from syringes and the like. These needle removal tools are not only convenient, but also provide a safe means for removal of the needle. The safe removal of the needle is essential to protect hospital personnel from certain injury and from contagious diseases.

Many prior disposable containers have had needle removal tools built into the top thereof adjacent the disposal opening. This is a convenient and desirable arrangement. However, the prior tools, while normally suitable for most applications, require rotation of the syringe barrel for removal of the needle. This is often inconvenient for the user, particularly if the container must be hand held. An example of an improved needle removal slot is disclosed in my U.S. Pat. No. 4,984,686, granted Jun. 15, 1991.

It is, therefore, desirable that an improved, convenient, and safe effective needle removal device be available.

SUMMARY AND OBJECTS OF THE INVENTION

It is the primary object of the present invention to provide an improved needle removal means for disposable containers.

In accordance with the primary aspect of the present invention, a needle removal device for a disposable container comprises an elongated slot, with a section of gear teeth along one side for engagement with flutes on the hub of a needle to rotate and unscrew the needle as it is passed therealong.

BRIEF DESCRIPTION OF THE DRAWING

The above and other objects and advantages of the present invention will become apparent from the following description when read in conjunction with the drawings wherein.

DETAILED DESCRIPTION OF A PREFERRED EMBODIMENT

Figure 1:
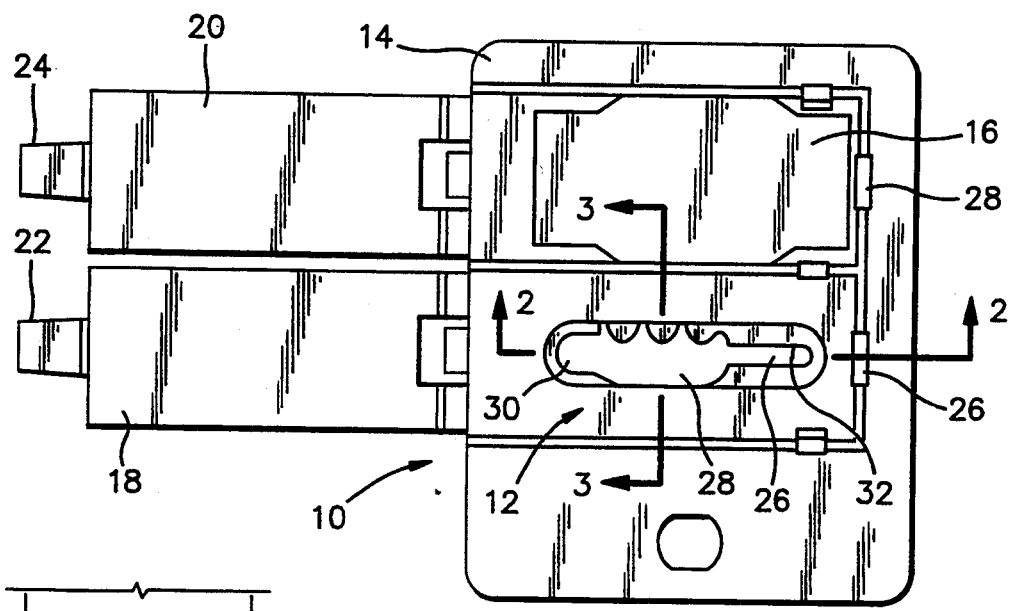
FIG. 1 is a top plan view of a closure assembly incorporating a preferred embodiment of the invention.

Referring now to the drawings and to particularly FIG. 1, there is illustrated a container closure assembly, designated generally by the numeral 10, which includes a needle removal device 12 constructed in accordance with a preferred embodiment of the invention. This closure assembly comprises a top support or frame member 12, which in the illustrated embodiment has a generally rectangular configuration for mounting on and covering the upwardly opening mouth or open top of a container (not shown). This top is permanently attached to a plastic type disposable container of the type typically used for the disposal of syringes, sharps and the like. These type containers are disclosed in a number of my previous patents, as will be mentioned.

The needle removal slot 12 is shown formed in a closure frame 14, which in the illustrated embodiment has a generally rectangular configuration, with an opening 16 for syringes, and covers 18 and 20 for the opening and the needle slot. The needle removal device may also be incorporated into any number of other container closure assemblies associated with various container closures, such as disclosed for example in my U.S. Pat. No. 4,984,686. These tops may be permanently attached to a plastic type disposable container of the type typically used for disposal of sharps, and other objects and the like, such as disclosed in a number of my previous patents.

The illustrated closure assembly is designed for use in conjunction with containers for the disposal of vacuum type syringes widely used for drawing of the blood samples. The closure comprises a rectangular panel 14, with an opening 16 for receiving spent syringes. Adjacent to the opening 16 is a removal device in accordance with the invention, designated generally by the numeral 12, for the removal of needles from the syringe body.

The opening 16 and the needle removal slot 12 are positioned within a rectangular recessed portion, as illustrated, with hinged cover members 18 and 20 hinged to one side of the top frame. The hinge covers 18 and 20 are shown pivoted to an open position, and each include locking tabs 22 and 24 for engaging slots 26 and 28 for latching in a permanently latched or closed position when the container is filled and ready for disposal.

Referring now specifically to the needle removal slot, it will be noted that the slot comprises a first or needle receiving portion 26, a second or intermediate and hub receiving portion 28, and an end or needle drop section 30. The overall slot is recessed downward into the closure frame assembly, as can be appreciated from FIGS. 2 and 3. The slot also opens directly into a container for direct disposal of needles.

The needle inlet slot portion 26 slopes downward from the upper surface of frame 14, with opposing parallel side walls 32 and 34 to the intermediate section 28.

The intermediate section 28 extends generally horizontally and is formed of a notched wall formed with teeth 36, 38 and 40 and a straight opposing wall 42. The opposing straight wall 42 biases against the hub radial flange and biases the flutes of the hub into the engagement with the teeth 36, 38 and 40, causing rotation of the hub and needle as a syringe is held against rotation and passed along the slot.

A terminal end of the slot 44 is formed of a continuation of side wall 42, which continues from an upper surface and an opposing side wall 44 above the teeth 36, 38 and 40 and the slot 32. The terminal end portion 46 of the slot extends beneath a generally C or horseshoe shaped hook or inwardly extending rim 48, which extends over and hooks the radially extending flange of a hub for exerting force to force it from the end of a barrel. The teeth 36, 38 and 40 step down slightly from the sloped slot 32 to the hook 48, permitting a hub flange to extend past beneath the hook 48. This also accommodates the unscrewing motion of the hub as it moves downward out of the end of a barrel, as depicted in FIG. 2.

The overall slot 12 is recessed below an upper surface of a support structure, such as a container top, so that there is provided support or spacer surfaces 48 and 50 which engage the end of a syringe barrel, and space the hub flutes to engage the intermediate portion of the slot and teeth, 36, 38 and 40. In particular, as illustrated in FIG. 2, a syringe barrel 52 shown in phantom has a neck 54 into which a needle hub is threaded. The end surface 52a of a barrel 52 engages the surfaces 48 and 50 surrounding or to each side of the slot, and permits the needle hub to extend down just sufficient to engage the gear teeth 36, 38 and 40.

As the hub unthreads from the end of the barrel, it moves downward as permitted by the downward stepped upper surfaces of the teeth 36, 38 and 40. At the end of the stroke, the flange of the hub extends beneath the horseshoe grip or hook 46 to give an axial force on the needle and hub assembly if needed.

Figure 2:
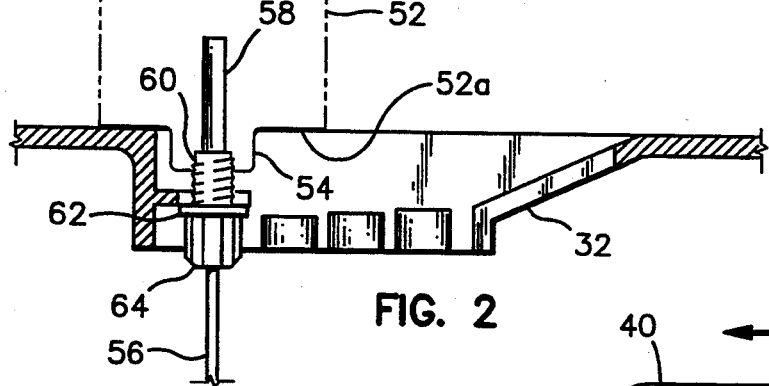
FIG. 2 is a sectional view taken on lines II—II of the closure assembly of FIG. 1.
Figure 3:
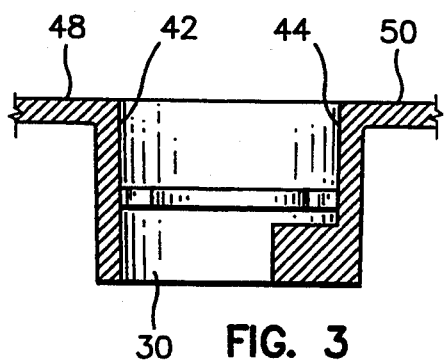
FIG. 3 is a sectional view taken on line III—III of FIG. 1.

As specifically illustrated in FIG. 2, a conventional needle assembly for the vacuum type containers includes a forward extending elongated needle 56 and an inwardly extending needle 58 which punctures the vacuum tube. A hub assembly includes an upper threaded portion 60, intermediate disk like flange 62 and forwardly extending flutes 64. The flutes are normally four in number but can serve or act roughly as a pinion gear, which cooperates with the tooth slot in a manner similar to rack gear or linear gear.

Figure 4:
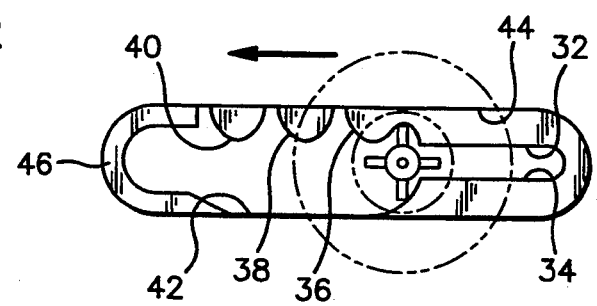
FIG. 4 is an enlarged detailed top plan view of the slot of FIG. 1 showing a needle hub engaged.
Figure 5:
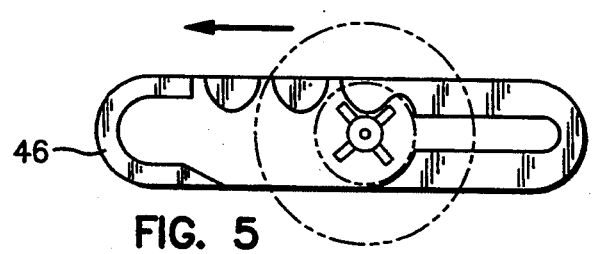
FIG. 5 is a view like FIG. 4 showing a still further position of the hub.
Figure 6:
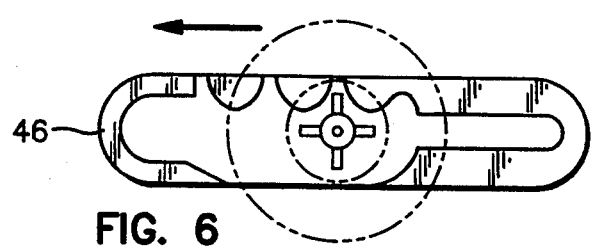
FIG. 6 is a view like FIG. 4 showing a still further position of the hub.

In operation, a syringe barrel 62 is grasped in the hand, and the needle 56 is inserted in slot 26 and permitted to slide downward, engaging flute 64 in the tooth section of the slot as the barrel is grasped and held against rotation and forced forward along the slot, as shown by arrows in FIGS. 4–6. As the barrel is moved forward along the slot, the flutes 64 engaging the teeth 36, 38 and 40 force the hub to rotate counter clockwise relative to the end of the syringe barrel, forcing it to unthread or unscrew from the neck 54 of the syringe barrel.

As the needle and hub assembly moves to the terminal end of the slot, the needle and hub assembly is permitted to fall from the end of the barrel. In case it is frictionally held in position, the horseshoe grip 46 may be engaged as the barrel is pulled upward, forcing the threaded portion of the needle hub from the end of the barrel neck 54. Thus, the needle is quickly, safely and effectively removed from the end of the syringe barrel.

While the needle slot is illustrated in the present example in conjunction with a specific disposable container top, it is to be understood that it may be utilized in conjunction with substantially any container top, such as disclosed in any number of my prior patents. It may also be used in conjunction with other needle slots, such as shown for example in my U.S. Pat. No. 4,984,684 and others.

While I have illustrated and described my invention by means of specific embodiments, it is to be understood that numerous changes and modifications may be made therein without departing from the spirit and scope of the invention as defined in the appended claims.

I claim:

1. A geared needle remover for use with disposable container assemblies comprising:
   closure frame means for mounting in an opening of a substantially rigid container;
   an opening in said frame means for receiving a disposable article; and
   needle removal slot means in said closure frame adjacent said opening, said slot means having gear teeth along one side thereof for engaging flutes on a needle hub for rotating said needle relative to a non-rotatable holder passed therealong.

2. A needle remover according to claim 1 wherein said needle removal slot means has an inlet portion of a width to accept a needle and exclude a hub, a geared portion of a width for accepting a fluted portion of a hub, and an end portion having a width for an entire hub to pass through.

3. A needle remover according to claim 1 wherein said needle removal slot means is disposed in a recess in said frame means and has a sloping needle inlet slot portion of a width to accept a needle and exclude a hub, an intermediate geared portion of a width for accepting a fluted portion of a hub with the flutes meshing with the gears, and an outlet end portion having a width for enabling an entire hub to pass through.

4. A needle remover according to claim 1 wherein said needle removal slot means is disposed in a recess in said closure frame means, and said frame means defines spacer means for engaging an end of a syringe barrel for positioning flutes on a needle in said gear teeth.

5. A needle remover according to claim 4 wherein said inlet slot portion slopes downward from said frame means to said intermediate portion in said recess.

6. A needle remover according to claim 4 wherein said outlet end portion has a horseshoe shaped wall spaced upward therefrom for the engagement and application of a force to a needle hub.

7. A needle remover according to claim 1 wherein:
   said opening and said needle removal slot means are disposed in rectangular recesses in said frame means;
   a first latch lock cover for covering said opening;
   a second latch lock cover means for covering said needle removal slot means; and
   said first and said second cover means each have a releasable latching mode and a permanent latching mode in said recesses.

8. A needle remover according to claim 7 wherein said needle removal slot means has an inlet portion of a width to accept a needle and exclude a hub, a geared portion of a width for accepting a fluted portion of a hub, and an end portion having a width sufficient for an entire hub to pass through.

9. A needle remover according to claim 8 wherein said needle removal slot means is disposed in a recess in said closure frame means, and said frame means defines spacer means for engaging an end of a syringe barrel for positioning flutes on a needle in said gear teeth.

10. A closure assembly for a disposable container, comprising:

frame means for mounting on an opening defined by a peripheral rim of a substantially rigid container;

an opening in said frame means for receiving a disposable article; and needle removal slot means in said frame means adjacent said opening and comprising an elongated slot defined by spaced apart opposed side walls, one of said side walls having gear teeth for engaging flutes on a needle hub, and the other side wall being substantially straight for biasing said flutes into said gear teeth for inducing rotation of a needle moved along said slot.

11. A closure assembly according to claim 10 wherein said needle removal slot means has an inlet portion of a width to accept a needle and exclude a hub, a geared portion of a width for accepting a fluted portion of a hub, and an end portion having a width for an entire hub to pass through.

12. A closure assembly according to claim 11 wherein said needle removal slot means is disposed in a recess in said closure frame means, and said frame means defines spacer means for engaging an end of a syringe barrel for positioning flutes on a needle in said gear teeth.

13. A closure assembly according to claim 12 wherein said inlet slot portion slopes downward from said frame means to said intermediate portion in said recess.

14. A closure assembly according to claim 13 wherein said outlet end portion has a horseshoe shaped wall spaced upward therefrom for the engagement and application of a force to a needle hub.

15. A closure assembly according to claim 14 wherein:

said opening and said needle removal slot means are disposed in rectangular recesses in said frame means;

a first latch lock cover for covering said opening;

a second latch lock cover means for covering said needle removal slot means; and said first and said second cover means each have a releasable latching mode and a permanent latching mode in said recesses.

16. A closure assembly for medical sharps container comprising:

frame means for mounting on an upwardly extending opening defined by a peripheral rim of a substantially rigid container;

an opening in said frame means for receiving a disposable article; and needle removal slot means in said frame means adjacent said opening and comprising an elongated slot having an inlet portion of a width for accepting a needle and excluding a hub, a geared portion having gear teeth and of a width for accepting a fluted portion of a hub, and an end portion having a width for an entire hub to pass through.

17. A closure assembly according to claim 16 wherein said needle removal slot means is disposed in a recess in said closure frame means, and said frame means defines spacer means for engaging an end of a syringe barrel for positioning flutes on a needle in said gear teeth.

18. A closure assembly according to claim 17 wherein said inlet slot portion slopes downward from said frame means to said intermediate portion in said recess.

19. A closure assembly according to claim 17 wherein said outlet end portion has a horseshoe shaped wall spaced upward therefrom for the engagement and application of a force to a needle hub.

20. A closure assembly according to claim 17 wherein:

said opening and said needle removal slot means are disposed in rectangular recesses in said frame means;

a first latch lock cover for covering said opening;

a second latch lock cover means for covering said needle removal slot means; and said first and said second cover means each have a releasable latching mode and a permanent latching mode in said recesses.

* * * * *